United States Patent
Sano

[11] Patent Number: 5,802,689
[45] Date of Patent: Sep. 8, 1998

[54] TUBE CONNECTING APPARATUS

[75] Inventor: Hiroaki Sano, Yamanashi-ken, Japan

[73] Assignee: Terumo Kabushiki Kaisha, Tokyo, Japan

[21] Appl. No.: 760,311

[22] Filed: Dec. 4, 1996

[30] Foreign Application Priority Data

Dec. 8, 1995 [JP] Japan .................................. 7-345561

[51] Int. Cl.$^6$ .............................. B21B 15/00; A61M 1/00
[52] U.S. Cl. ...................... 29/33 T; 156/159; 156/304.2; 156/503; 604/905
[58] Field of Search .................................. 29/33 D, 33 T; 219/243, 221; 156/159, 304.2, 433, 503, 512; 83/171; 604/905

[56] References Cited

U.S. PATENT DOCUMENTS

| 4,369,779 | 1/1983 | Spencer | 604/29 |
|---|---|---|---|
| 4,412,835 | 11/1983 | Spencer | 604/29 |
| 4,516,971 | 5/1985 | Spencer | 604/280 |
| 4,521,263 | 6/1985 | Benin et al. | 156/159 |
| 4,610,670 | 9/1986 | Spencer | 604/29 |
| 4,619,642 | 10/1986 | Spencer | 604/29 |
| 4,753,697 | 6/1988 | Shaposka et al. | |
| 4,793,880 | 12/1988 | Shaposka et al. | 156/503 |
| 4,913,756 | 4/1990 | Shaposka et al. | 156/503 |
| 4,933,036 | 6/1990 | Shaposka et al. | 156/503 |
| 5,141,592 | 8/1992 | Shaposka et al. | 156/515 |
| 5,244,522 | 9/1993 | Spencer et al. | 156/304.2 |
| 5,279,685 | 1/1994 | Ivansons et al. | 156/503 |
| 5,502,293 | 3/1996 | Ohnishi et al. | 219/543 |
| 5,518,575 | 5/1996 | Watanabe | 156/503 |
| 5,554,253 | 9/1996 | Watanabe | 156/304.2 |

FOREIGN PATENT DOCUMENTS

| 0 044 204 | 1/1982 | European Pat. Off. |
|---|---|---|
| 0 105 587 | 4/1984 | European Pat. Off. |
| 0 471 953 | 2/1992 | European Pat. Off. |
| 0 483 478 | 5/1992 | European Pat. Off. |
| 0 515 811 | 12/1992 | European Pat. Off. |
| 0 583 582 | 2/1994 | European Pat. Off. |
| 0 619 175 | 10/1994 | European Pat. Off. |
| 0 507 321 | 6/1995 | European Pat. Off. |
| 0 734 840 | 10/1996 | European Pat. Off. |
| 61-30582 | 7/1986 | Japan . |
| 4-308731 | 10/1992 | Japan . |

*Primary Examiner*—A. L. Pitts
*Assistant Examiner*—Christopher Kirkman
*Attorney, Agent, or Firm*—Burns, Doane, Swecker & Mathis, LLP

[57] ABSTRACT

A tube connecting apparatus includes first and second tube holders holding flexible tubes, a cutting blade for heating, melting and cutting the tubes held by the holders between the holders, and a holder displacing mechanism for relatively displacing the second holder to the first holder to closely contact and connect cutting ends of the tubes each other. Each of the first and second tube holders has a tube holding portion which holds the tubes in a state that the circular cylindrical surfaces of the tubes which are contacting each other.

13 Claims, 11 Drawing Sheets

TUBE CONNECTING APPARATUS

BACKGROUND OF THE INVENTION

1. Field of the Invention

This invention relates to a tube connecting apparatus which heats and melts a plurality of tubes having flexibility to be cut and connects the respective cut ends of the tubes each other in a sterile condition.

2. Description of the Related Art

This kind of tube connecting apparatus has already been known from, e.g., Japanese Patent Application KOKOKU Publication No. 61-30582 and Japanese Patent Application KOKAI Publication No. 4-308731.

Japanese Patent Application KOKOKU Publication No. 61-30582 discloses a tube connecting apparatus which includes a pair of holders (first and second holders) for holding two tubes in parallel to each other and a cutting blade (plate-like heating element) being arranged between both holders to be movable to cross the tubes. Two grooves are formed in each of the holders, and the two pairs of the grooves of the two holders are aligned on two straight lines. One end portion of the first tube is held in the first groove of the first holder and the first groove of the second holder. The first tube is extended from that side of the first holder which is opposite to the second holder. One end portion of the second tube is held in the second groove of the first holder and the second groove of the second holder. The second tube is extended from that side of the second holder which is opposite to the first holder. The heated cutting blade is moved from its retracted position to its cutting position, and heats and melts the two tubes to be cut at a portion between the both holders. Thereafter, the first holder is moved in a direction in which the two tubes are arranged, so that cut ends of main bodies of the two tubes are arranged to be coaxial to each other. Moreover, the cutting blade is moved to the retracted position, so that the cut ends of the main bodies of the two tubes are melted and connected together.

In the tube connecting apparatus of Japanese Patent Application KOKOKU Publication No. 61-30582, if an operator makes a mistake so that the tubes are set in wrong grooves of the paired holders, the cut ends of the main bodies of the two tubes are not connected together but the cut ends of the end portions of the two tubes are connected to each other. The operator must pay his attention to the operation of the tube connecting apparatus. As a result of this, operability of the tube connecting apparatus is low.

Japanese Patent Application KOKAI Publication No. 4-308731 also discloses a tube connecting apparatus which includes a pair of holders (first and second holders) for holding two tubes in parallel to each other and a cutting blade (plate-like heating element) being arranged between both holders to be movable to cross the tubes. In this tube connecting apparatus, two grooves are also formed in each of the holders, and the two pairs of the grooves of the two holders are aligned on two straight lines. Similar to Japanese Patent Application KOKOKU Publication No. 61-30582, two tubes are held at two grooves of each of the holders. In the tube connecting apparatus of Japanese Patent Application KOKAI Publication No. 4-308731, the heated cutting blade is moved from its retracted position to its cutting position, and heats and melts the two tubes to be cut at a portion between the both holders. Thereafter, the first holder is revolved through 180° around an intermediate position between the two grooves, so that cut ends of main bodies of the two tubes are arranged to be coaxial to each other while cut ends of end portions of the two tubes are also arranged to be coaxial to each other. Then, the cutting blade is moved to the retracted position, so that the cut ends of the main bodies of the two tubes are melted and connected together, and the cut ends of the end portions of the two tubes are melted and connected together.

In the tube connecting apparatus of Japanese Patent Application KOKAI Publication No. 4-308731, it is advantages that the two tubes can be connected to each other without leaking liquid therefrom even if liquid is left in an inner hole of at least one of the two tubes before it is not cut.

In these conventional tube connecting apparatus, each of the pair of the holders holds two tubes to be spaced from each other with a predetermined distance therebetween. Due to this, after the two tubes are cut by the cutting blade, one tube must be moved for a relatively long distance to arrange the cut end of its main portion coaxial with the cut end of the main portion of the other tube. Particularly, in the conventional tube connecting apparatus of Japanese Patent Application KOKAI Publication No. 4-308731, the diameter of the locus of the cut end of the first tube, the locus being drawn when the first holder is revolved to arrange the cut ends of the two tubes to be coaxial to each other, corresponds to a distance between the two tubes. Since the cut end of the main body of each tube and that of the end portion thereof must be contacting the cutting blade while the first holder is being revolved, the outer size of the cutting blade is inevitably enlarged, so that the outer size of the tube connecting apparatus is inevitably enlarged.

An object of the present invention is to provide a tube connecting apparatus in which a displacement of each tube, which is necessary for connecting a plurality of tubes to each other, is small so that structural elements of the tube connecting apparatus and hence the tube connecting apparatus itself can be miniaturized.

SUMMARY OF THE INVENTION

In order to achieve the above object, a tube connecting apparatus according to this invention, comprising: first and second tube holders each of which holds a plurality of tubes having flexibility; a cutting device for heating, melting and cutting the tubes held by the first and second tube holders between the first and second tube holders; and a tube holder displacing device for relatively displacing the second tube holder to the first tube holder to closely contact and connect cutting ends of the tubes cut by the cutting device, each other, wherein each of the first and second tube holders has a tube holding portion which holds the plurality of the tubes in a state that the circular cylindrical surfaces of the tubes which are contacting with each other.

According to the above-mentioned structure of the tube connecting apparatus of this invention, the tube holding portion of each of the first and second holders holds the plurality of the tubes in a state that the surfaces of the tubes which are contacting with each other. As a result of this, the displacement space of one of the first and second tube holders relative to the other, that is, the displacement space of each of the plurality of the tubes relative to each other, which is necessary to connect the cutting ends of the tubes each other, may be small.

Therefore, the outer size of some of structural elements of the tube connecting apparatus such as the cutting device can be minimized, and hence the body size of the tube connecting apparatus can be minimized as compared with the conventional connector. Moreover, the positional difference between the cutting ends of the plurality of the tubes can be reduced when connecting the plurality of the cutting ends of the tubes each other. As a result of this, the connecting accuracy of the plurality of the cutting ends and the connecting strength thereof can be improved.

In the tube connecting apparatus of the present invention characterized by being structured as described above, the tube holding portion preferably includes a groove for receiving the plurality of the tubes which are overlapped with each other.

According to this structure, it is only needed to insertion the plurality of the tubes into the same groove in order to mount the tubes in the tube holding portion, so that an operator will not mistake mounting order and/or arrangement of the tubes and the operability of the tube connecting apparatus is better than the above described conventional connector.

In the tube connecting apparatus of the present invention characterized by being structured as described above, the tube holding portion preferably holds the plurality of the tubes in a state that the circular cylindrical surfaces of the tubes which are contacting with each other so that the inner holes of the tubes are flattened.

In this case, the distance between the plurality of the tubes is further reduced. Therefore, the displacement space of one of the first and second tube holders relative to the other, that is, the displacement space of each of the plurality of the tubes, which is necessary to connect the plurality of cut ends of the tubes to each other.

As a result of this, the outer size of some of the structural elements of the tube connecting apparatus such as the cutting device, and the body size of the tube connecting apparatus can be further minimized as compared with the conventional connector. Moreover, the positional difference between the cut ends of the plurality of the tubes can be further reduced when connecting the cut ends of the tubes each other. Then, the connecting accuracy of the plurality of the cut ends and the connecting strength thereof can be further improved.

Further, since the cut ends are not opened, no liquid is leaked from the inner hole of each of the tubes until the connection of the cut ends of the plurality of the tubes is finished, even if liquid exists in the inner hole of each of the tubes.

In a case that each of the plurality of the tubes to be connected each other is held in each of the tube holding portions in a state that each of the inner holes is flattened, each of the tube holding portions preferably includes a groove for receiving the plurality of the tubes which are overlapped with each other, and a flattening device for flattening the tubes in the groove.

In the tube connecting apparatus of this invention characterized by being structured as described above, the tube holder displacing device preferably includes a holder rotating mechanism for rotating the second tube holder relative to the first tube holder around a center line which passes through an intermediate position of the plurality of the tubes held by each holder and extends in the extending direction of the plurality of the tubes.

In this case, the tube holder displacing device revolves the second tube holder relative to the first tube holder through 180°, so that the cut ends of the plurality of the tubes of the second tube holder are rotated around the above described center line through 180° relative to the cut ends of the plurality of the tubes of the first tube holder to be aligned each other.

The tube holder displacing device preferably has a holder approaching mechanism for shortening the distance between the first and second tube holders after the second tube holder is revolved relative to the first tube holder so that the cut ends of the plurality of the tubes of the first holder and those of the second tube holder are closely in contact with each other.

Such a holder approaching mechanism as described above reinforces the connection between the cut ends of the plurality of the tubes of the first holder and those of the second holder.

The cutting device preferably includes a cutting blade heated at high temperatures for melting and cutting the plurality of the tubes, and a cutting blade moving device for inserting and retracting the cutting blade to and from a gap between the first and second tube holders.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

The first and second embodiments of the tube connecting apparatus will be explained in detail with reference to the accompanying drawings.

DETAILED DESCRIPTION OF THE PREFERRED EMBODIMENTS

[First embodiment]

The first embodiment of the tube connecting apparatus of the present invention will be explained in detail with reference to FIGS. 1 to 5.

Figure 1:
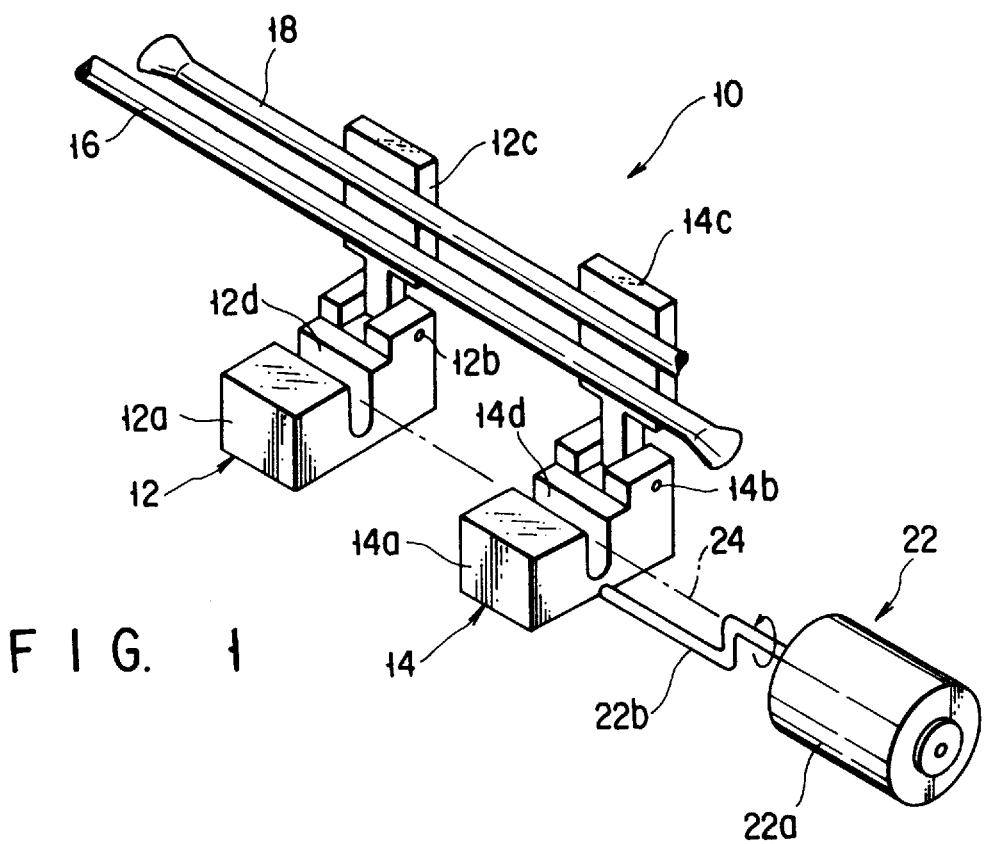
FIG. 1 is a perspective view showing a main part of a first embodiment of the tube connecting apparatus of this invention.

FIG. 1 is a perspective view showing the main part of the first embodiment of the tube connecting apparatus of this invention. FIGS. 2 to 5 are perspective views each showing the tube mounted state, the tube cut state, the tube rotated and connected state, and the tube discharge state in the tube connecting process which uses the tube connecting apparatus of FIG. 1.

As shown in these figures, a tube connecting apparatus 10 according to the first embodiment of the present invention includes a first tube holder 12, a second tube holder 14, cutting means 20, and tube holder displacing means 22. The cutting means 20 selectively heats and melts two tubes 16 and 18 which are formed of soft resin such as soft polyvinyl chloride and which have flexibility, to cut them. The tube holder displacing means 22 revolves the second tube holder 14 relative to the first tube holder 12 in a predetermined direction through 180°. In FIGS. 1 and 5, the cutting means 20 is omitted, and in FIGS. 2 to 5, the tube holder displacing means 22 is omitted.

The first tube holder 12 has a holder body 12a which holds the two tubes 16 and 18, and a cover 12c. The cover 12c is attached by a hinge 12b to a rear end portion of the holder body 12a to be freely rotatable between an open position and a closed position relative to an upper surface of the holder body 12a. On the upper surface of the holder body 12a, a groove 12d is formed. The groove 12d has a U-shaped cross section, and serves as a tube holding portion which holds the two tubes 16 and 18 in a state that they are stacked vertically with their peripheral surfaces being in contact with each other.

The width of the groove 12d is preferably equal to or less than the diameter of each of the tubes 16 and 18 in their natural state. In the latter case, the tubes 16 and 18 are inserted into the groove 12d after they are pulled to reduce their outer diameters or are forcibly pushed into the groove 12d.

In this embodiment, it is desirable that the outer and inner diameters of the first tube 16 and those of the second tube 18 are substantially the same as each other.

Figure 2:
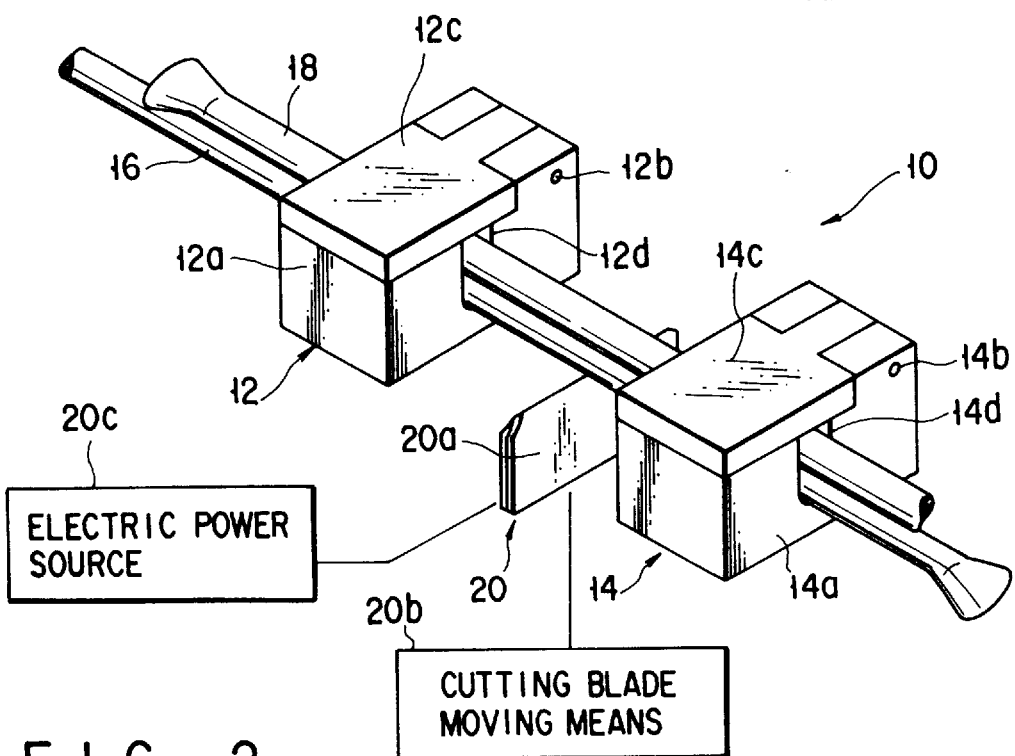
FIG. 2 is a perspective view showing a tube mounted state in a tube connecting process which uses the tube connecting apparatus of FIG. 1.

The cover 12c is freely rotatable between an open position and a closed position. In the open position, as shown in FIG. 1, the cover 12c is spaced apart from the upper surface of the holder body 12a to open an upper opening of the groove 12d. In the closed position, as shown in FIG. 2, the cover 12c is overlaid on the upper surface of the holder body 12a to close the upper opening of the groove 12d. The cover 12c may be selectively urged to the open position or the closed position by a well known selection urging means (not shown) such as a toggle spring. Also, the cover 12c may be selectively temporarily fixed at the open position or the closed position by a well known temporarily fixing means (not shown).

The structure of the second tube holder 14 is the same as that of the first tube holder 12. Specifically, the second tube holder 14 has a holder body 14a which holds the two tubes 16 and 18, and a cover 14c which is attached by a hinge 14a to a rear end portion of the holder body 14a to be freely rotatable between an open position and a closed position relative to the upper surface of the holder body 14a. On the upper surface of the holder body 14a, a groove 14d is formed. The groove 14d has a U-shaped cross section, and serves as a tube holding portion which holds the two tubes 16 and 18 in a state that they are stacked vertically with their peripheral surfaces being in contact with each other.

The width of the groove 14d also preferably equal to or less than the diameter of each of the tubes 16 and 18 in their natural state.

The cover 14c is also freely rotatable between an open position and a closed position. In the open position, as shown in FIG. 1, the cover 14c is spaced apart from the upper surface of the holder body 14a to open the upper opening of the groove 14d. In the closed position, as shown in FIG. 2, the cover 14c is overlaid on the upper surface of the holder body 14a to close the upper opening of the groove 14d. The cover 14c also may be selectively urged to the open position or the closed position by a well known selection urging means (not shown) such as a toggle spring. Further, the cover 14c may be selectively temporarily fixed at the open position or the closed position by a well known temporarily fixing means (not shown).

The first and second holders 12 and 14 are so arranged that the grooves 12d and 14d are aligned on a straight line at the same level as to each other in the vertical direction.

As shown in FIG. 2, the cutting means 20 has a cutting blade 20a which is located between the first and second tube holders 12 and 14, and a well known cutting blade moving means 20b which is connected to the cutting blade 20a. The cutting blade moving means 20b selectively moves the cutting blade 20a between a lower position (retracted position) and an upper position (cutting position). In the lowered or retracted position, the cutting blade 20a is moved downward from a gap between the first and second tube holders 12 and 14, and in the upper position the cutting blade 20a is inserted into the gap between the first and second holders 12 and 14 so as to cross a center line 24 (FIG. 1) passing through a center of the groove 12d of the first holder 12 and that of the groove 14d of the second holder 14.

In this embodiment, the cutting blade 20a is a self-heat generating type, and is structured by, for example a folded copper plate sandwiching an electric resistance through an insulating material. The electric resistance is connected to an electric power source 20c.

The cutting blade 20a is preferably replaced with new one at every time when it is used in one tube cutting work.

The cutting blade 20a may be heated by an outer heating means such as an electric heater or a high frequency heating means.

As is shown in FIG. 1, the tube holder displacing means 22 has a motor 22a which is positioned at that side of the second tube holder 14 opposite to the first tube holder 12, and a crank shaft 22*b* which is coupled to an output shaft of the motor 22*a*. The output shaft of the motor 22*a* is arranged to be coaxial with the center line 24 of the grooves 12*d* and 14*d* of the first and second holders 12 and 14 and an extended end of the crank shaft 22*b* is fixed to that outer side surface of the second tube holder 14 opposite to the first tube holder 12.

Any motor which can selectively rotates its output shaft through 180° in one direction and the other direction can be used as the motor 22*a*. For this reason, a DC motor or a step motor, each of which is capable of controlling the rotation angle of the output shaft, is preferably used as the motor 22*a*.

In the following, a process for connecting the two tubes 16 and 18 to each other at their positions close to their extended ends by the above-structured tube connecting apparatus according to the first embodiment of this invention.

At first, the covers 12*c* and 14*c* of the first and second tube holders 12 and 14 are located in their open positions as shown in FIG. 1, and the cutting blade 20*a* of the cutting means 20 is located in its lower position (retracted position). During this time, the extended end portions of the two tubes 16 and 18 are inserted into the grooves 12*d* and 14*d* of the first and second tube holders 12 and 14 with their extended ends being overlapped or stacked with each other, as shown in FIG. 1. Then, a main body of the first tube 16 is extended from the first tube holder 12 in a direction opposite to the second tube holder 14, and a main body of the second tube 18 is extended from the second tube holder 14 in a direction opposite to the first tube holder 12.

In this embodiment, each of the extended end portions of the first and second tubes 16 and 18 is sealed by, for example heating and melting it.

The center line 24 of the grooves 12*d* and 14*d* are positioned at an intermediate position between the two tubes 16 and 18 in the grooves 12*d* and 14*d*.

Then, the covers 12*c* and 14*c* of the first and second tube holders 12 and 14 are rotated to their closed positions as shown in FIG. 2, prevent the two tubes 16 and 18 from being dropped off from the upper opening of the groove 12*d* and that of the groove 14*d*, and keep the tubes 16 and 18 in that state in which their peripheral surfaces are in contact with each other in the grooves 12*d* and 14*d*.

Next, the cutting blade 20*a* which has been heated by the electric power source 20*c* in advance, is moved from the lower position (retracted position) to the upper position (cutting position) by the cutting blade moving means 20*b*. At this time, the cutting blade 20*a* melts and cuts the tubes 16 and 18 as shown in FIG. 3.

The motor 22*a* (FIG. 1) of the tube holder displacing means 22 rotates the output shaft through 180° in a predetermined direction (counterclockwise in FIG. 1). As result of this, the second tube holder 14 which is coupled to the output shaft of the motor 22*a* through the crank shaft 22*b* (FIG. 1), is revolved around the center line 24 of the grooves 12*d* and 14*s* through 180° in a predetermined direction (counterclockwise in FIG. 2) from the state shown in FIG. 2, so that, the second tube holder 14 is upside down in comparison with the first tube holder 12 as shown in FIG. 3.

Since the center line 24 of the grooves 12*d* and 14*d* of the first and second tube holders 12 and 14 is positioned at the intermediate position between the two tubes 16 and 18 in the grooves 12*d* and 14*d*, a cut end of the main body of the second tube 18 which is held by the groove 14*d* of the second tube holder 14, is arranged to be coaxial with a cut end of the main body of the first tube 16 which is held by the groove 12*d* of the first tube holder 12, and a cut end of the extended end portion 16*a* of the first tube 16 which is held by the groove 14*d* of the reversed second tube holder 14, is arranged to be coaxial with a cut end of the extended end portion 18*a* of the second tube 18 which is held by the groove 12*d* of the first tube holder 12.

Figure 3:
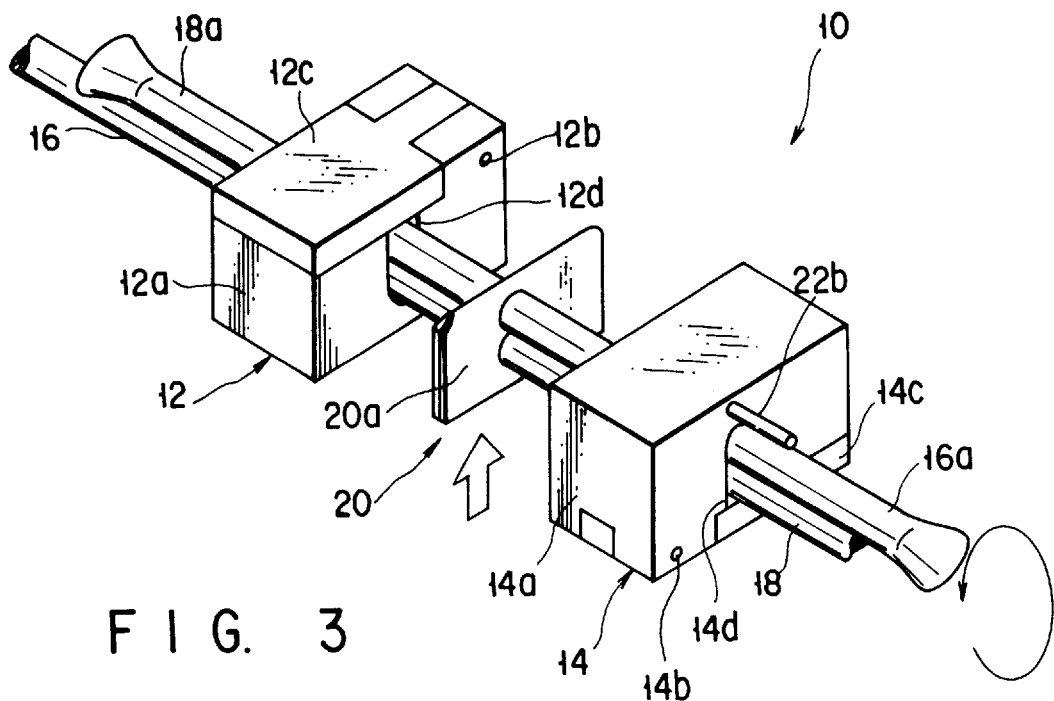
FIG. 3 is a perspective view showing a tube cut state sequent to the tube mounted state of FIG. 2 in the tube connecting process which uses the tube connecting apparatus of FIG. 1.
Figure 4:
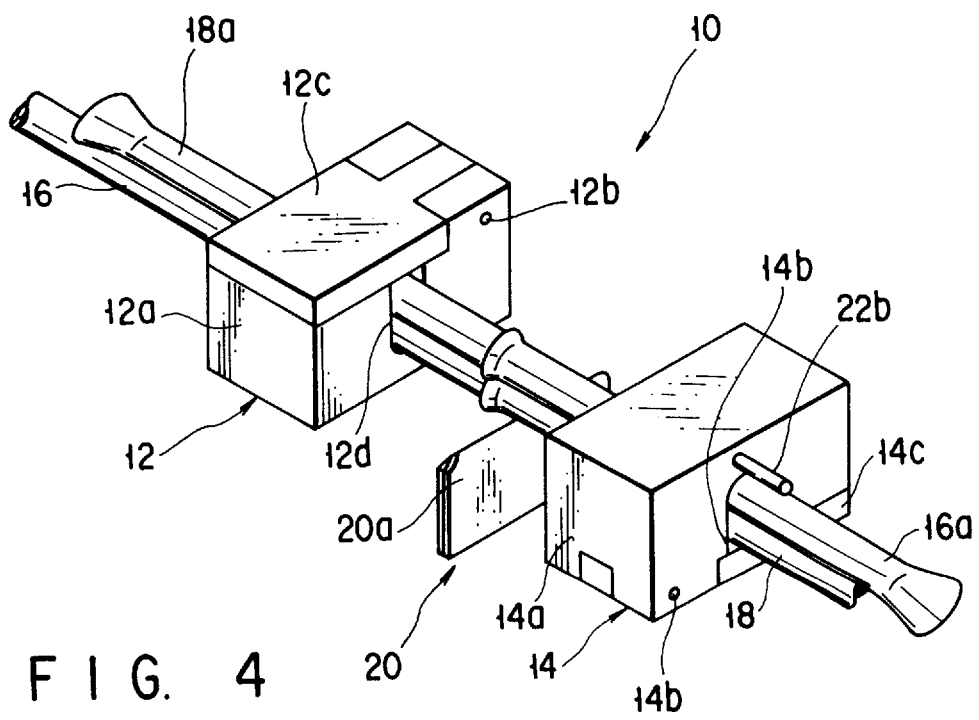
FIG. 4 is a perspective view showing a tube rotated and connected state sequent to the tube cut state of FIG. 3 in the tube connecting process which uses the tube connecting apparatus of FIG. 1.
Figure 5:
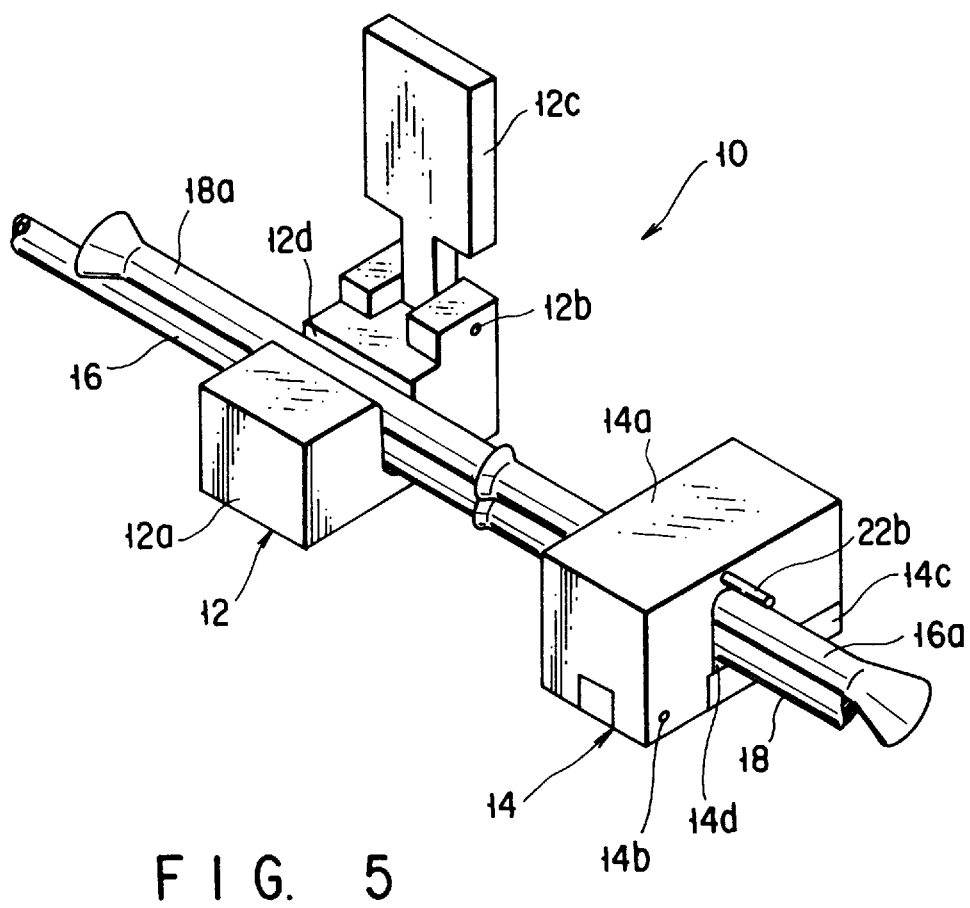
FIG. 5 is a perspective view showing a tube discharge state in the tube connecting process which uses the tube connecting apparatus of FIG. 1.

Then, the cutting blade 20*a* is moved from the upper position (cutting position) of FIG. 3 to the lower position (retracted position) of FIG. 4 by the cutting blade moving means 20*b*. At this time, the melted cut-end of the main body of the first tube 16 which is held by the groove 12*d* of the first tube holder 12, is connected to the melted cut-end of the main body of the second tube 18 which is held by the groove 14*d* of the second tube holder 14, and also the melted cut-end of the extended end portion 18*a* of the second tube 18 which is held by the groove 12*d* of the first tube holder 12, is connected to the melted cut-end of the extended end portion 16*a* of the first tube 16 which is held by the groove 14*d* of the reversed second tube holder 14.

Taking out of the main bodies of the tubes 16 and 18 connected to each other and the extended end portions 16*a* and 18*a* of the tubes 16 and 18 connected to each other from the grooves 12*d* and 14*d* will be performed as follows.

Firstly, only the cover 12*c* of the first tube holder 12 is rotated to the open position, and the main bodies of the tubes 16 and 18 connected to each other and the extended end portions 16*a* and 18*a* of the tubes 16 and 18 connected to each other are taken out from only the groove 12*d* of the first tube holder 12.

Next, the second tube holder 14 is revolved through 180° in a clockwise direction from the reversed position of FIG. 4 to be returned to the initial position of FIG. 1 while the second tube holder 14 holds the main bodies of the tubes 16 and 18 connected to each other and the extended end portions 16*a* and 18*a* of the tubes 16 and 18 connected to each other in the groove 14*d*.

Finally, the cover 14*c* of the second tube holder 14 is rotated to the open position, and the main bodies of the tubes 16 and 18 connected to each other and the extended end portions 16*a* and 18*a* of the tubes 16 and 18 connected to each other are taken out from only the groove 14*d* of the second tube holder 14.

Since the extended end portions 16*a* and 18*a* of the tubes 16 and 18 connected to each other are not necessary, they are discarded. In this case, these extended end portions 16*a* and 18*a* of the tubes 16 and 18 connected each other, can reduce a possibility that the discarded end portions 16*a* and 18*a* will be scattered around the tube connecting apparatus as compared with a case in which the end portions 16*a* and 18*a* of the tubes 16 and 18 are not connected each other.

The main bodies of the tubes 16 and 18 connected each other and the end portions 16*a* and 18*a* thereof connected each other can also be taken out from the grooves 12*d* and 14*d* as follows.

At first, the covers 12*c* and 14*c* are rotated to the open position as shown in FIG. 5. Then, the main bodies of the tubes 16 and 18 connected each other and the end portions 16*a* and 18*a* of the tubes 16 and 18 connected each other are taken out from the both grooves 12*d* and 14*d* while the second tube holder 14 is reversed.

In this time, the cutting blade 20*a* which has been located in the lower position (retracted position) of FIG. 4, does not prevent the main bodies of the tubes 16 and 18 connected each other and the end portions 16*a* and 18*a* of the tubes 16 and 18 connected each other from being taken out from the both grooves 12*d* and 14*d*.

Finally, the second tube holder 14 is revolved by the crank shaft 22*b* coupled to the output shaft of the motor 22*b* of the tube holder displacing means 22 of FIG. 1, through 180° in a clockwise direction from the reversed position of FIG. 4 to be returned to the initial position of FIG. 1.

[Second embodiment]

Next, the second embodiment of the tube connecting apparatus of the present invention will be explained in detail with reference to FIGS. 6 to 15.

Figure 6:
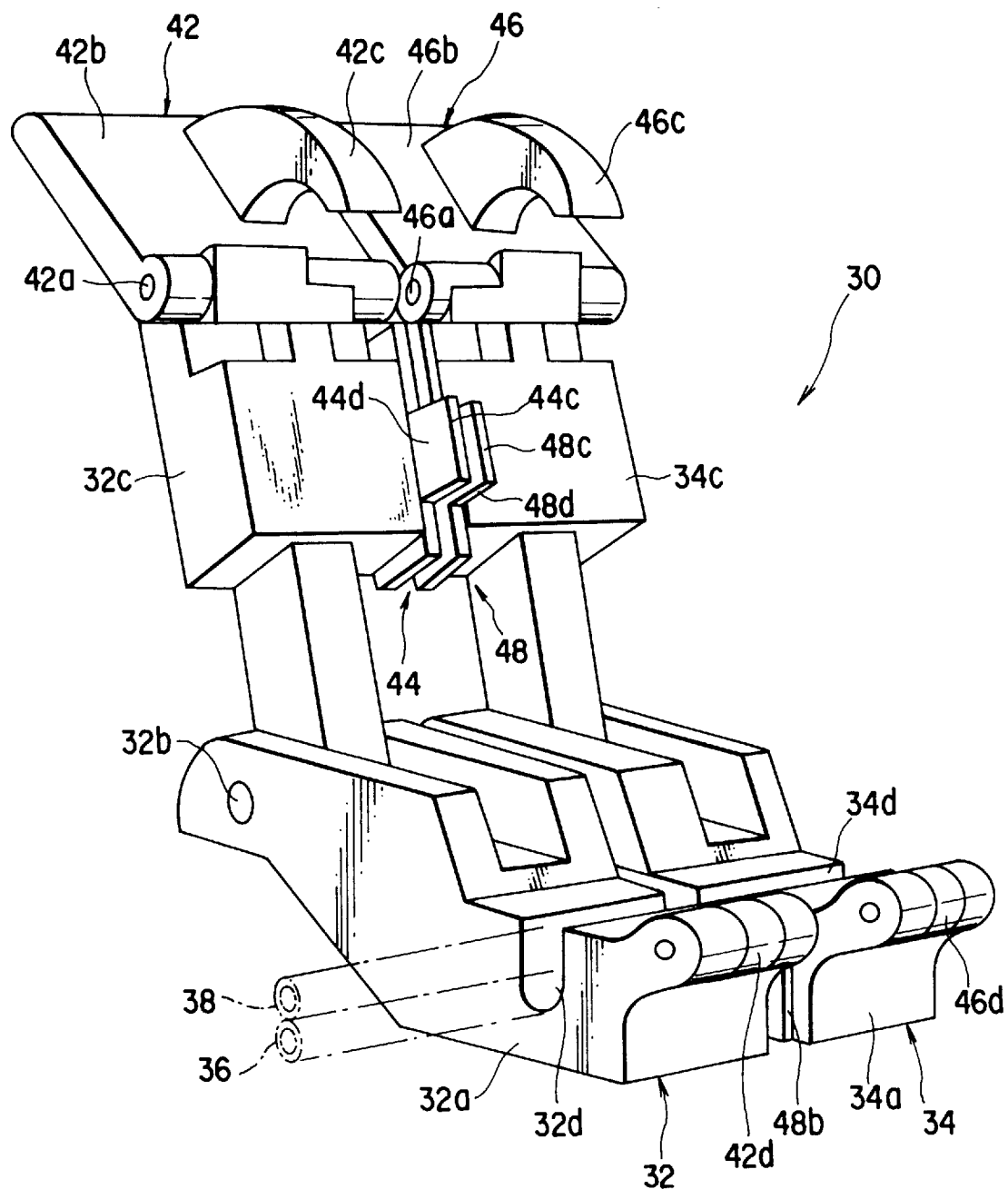
FIG. 6 is a perspective view showing a main part of a second embodiment of the tube connecting apparatus of the present invention.
Figure 7:
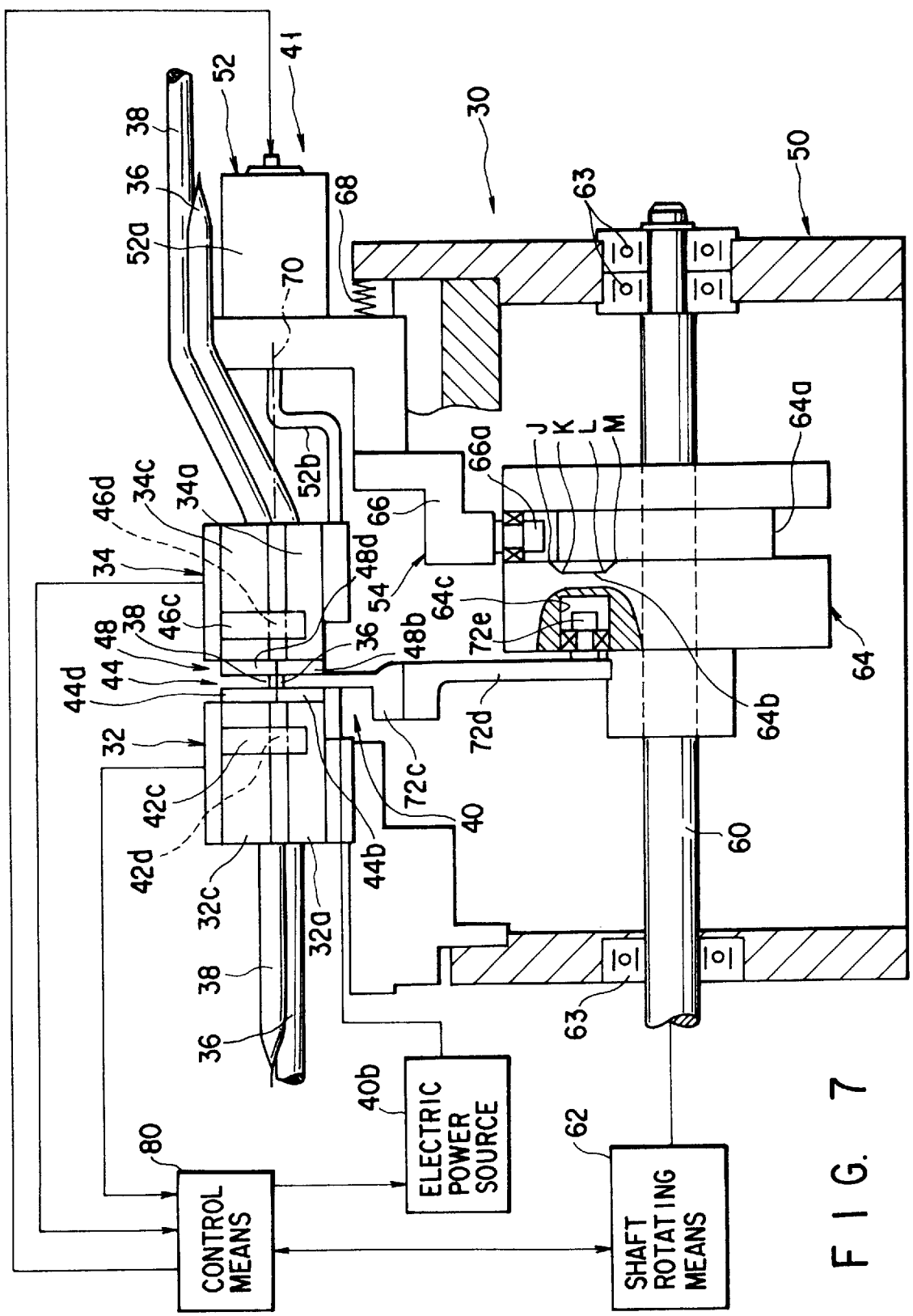
FIG. 7 is a front view showing a whole structure of the tube connecting apparatus of FIG. 6, with a part of which being sectioned.
Figure 8:
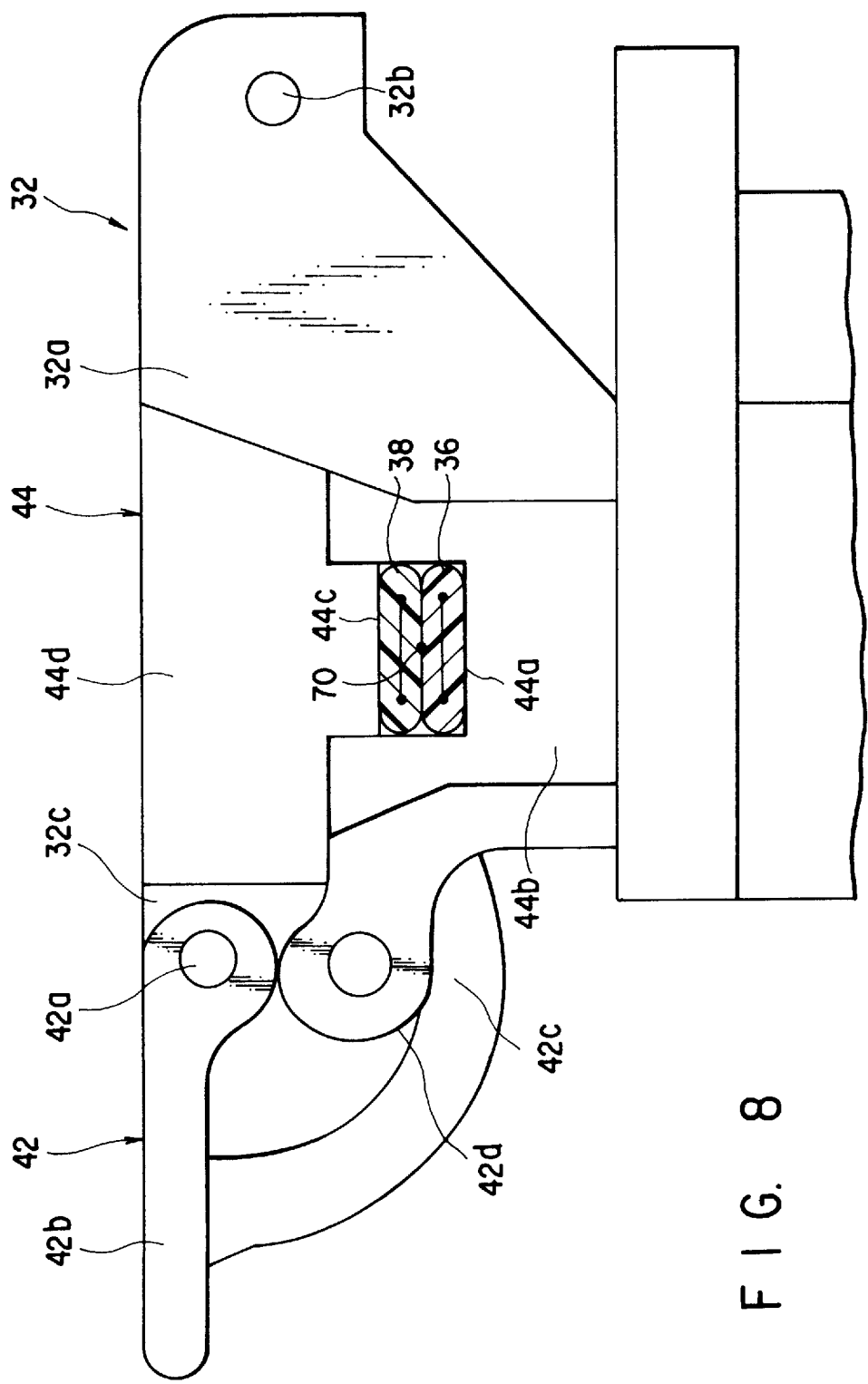
FIG. 8 is a side view showing a first tube holder of the tube connecting apparatus of FIG. 6 in a state that the first tube holder holding the two tubes.
Figure 9:
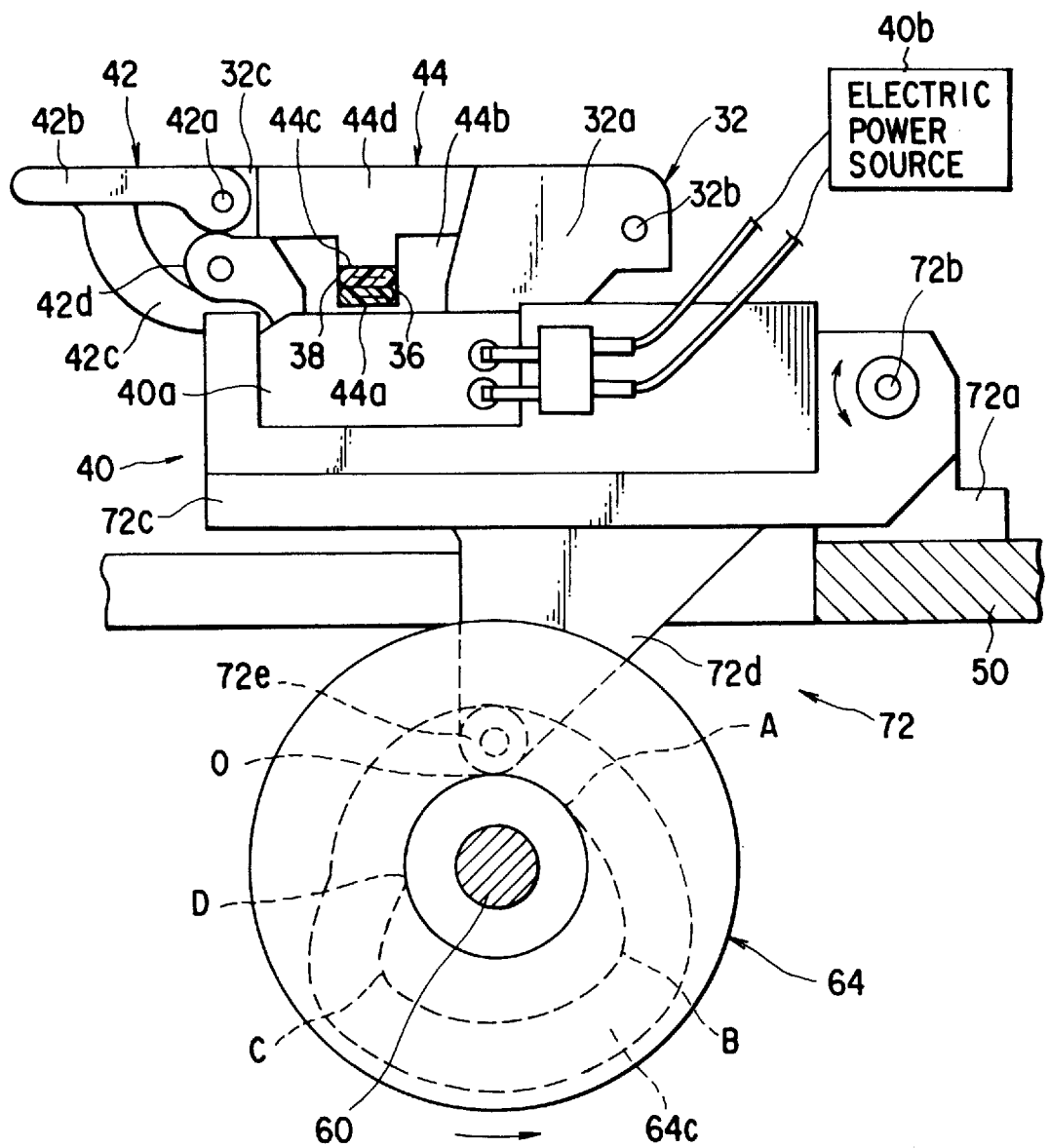
FIG. 9 is a side view showing the structure of cutting means of the tube connecting apparatus of FIG. 6.

FIG. 6 is a perspective view showing a main portion of the second embodiment of the tube connecting apparatus of the present invention. FIG. 7 is a front view showing a whole structure of the tube connecting apparatus of FIG. 6, with a part of which being sectioned. FIG. 8 is a side view showing a first tube holder of the tube connecting apparatus of FIG. 6 in a state that the first tube holder holding two tubes. And, FIG. 9 is a side view showing a structure of cutting means of the tube connecting apparatus of FIG. 6.

As shown in FIGS. 6 and 7, a tube connecting apparatus 30 according to the second embodiment of this invention includes a first tube holder 32, a second tube holder 34, cutting means 40, and tube holder displacing means 41. The cutting means 40 selectively heats and melts two tubes 36 and 38 which are formed of soft resin such as soft polyvinyl chloride and which have flexibility, to cut them. The tube holder displacing means 41 revolves the second tube holder 34 relative to the first tube holder 32 in a predetermined direction through 180°.

The first and second tube holders 32 and 34 are arranged adjacently to each other and have the same structure as to each other.

The first tube holder 32 has a holder body 32a which holds the two tubes 36 and 38, and a cover 32c which is attached by a hinge 32b to a rear end portion of the holder body 32a to be freely rotatable relative to an upper surface of the holder body 32a between an open position and a closed position. On the upper surface of the holder body 32a, a groove 32d is formed. The groove 32d has a U-shaped cross section, and serves as a tube holding portion which holds the two tubes 36 and 38 in a state that the two tubes 36 and 38 are stacked vertically with their peripheral surfaces being in contact with each other.

The width of the groove 32d is preferably equal to the maximum width of each of the tubes 36 and 38, which is obtained when each of these tubes is pressed. Also, in the embodiment, it is desirable that the inner and outer diameters of the first tube 36 and those of the second tube 38 are substantially the same as to each other.

In the open position, as shown in FIG. 6, the cover 32c is spaced apart from an upper surface of the holder body 32a to open an upper opening of the groove 32d. In the closed position, the cover 32c is overlaid on the upper surface of the holder body 32a to close the upper opening of the groove 32d. The cover 32c may be selectively urged to the open position or the close position by a well known selection urging means (not shown) such as a toggle spring. Also, the cover 32c may be selectively temporarily fixed at the open position or the closed position by a well known temporarily fixing means (not shown).

In this embodiment, the cover 32c is provided with locking means 42 for locking the cover 32c at the closed position. The locking means 42 has a locking plate 42b, a locking claw 42c, and a claw engaging member 42d. The locking plate 42b is attached by a hinge 42a to a free end of the cover 32c to be freely rotatable. The locking claw 42c is provided on an inner surface of the locking plate 42b. The claw engaging member 42d is provided on a front surface of the holder body 32a.

Moreover, in this embodiment, the cover 32c is provided with flattening means 44 for pressing and flattening the two tubes 36 and 38 which are held in the groove 32d of the holder body 32a of the first tube holder 32, at an inner side opening of the groove 32d which faces the second tube holder 34, in the upper and lower directions so as to close the inner hole of each of the tubes 36 and 38.

As particularly shown in FIG. 8, the flattening means 44 has a first pressing plate 44b and a second pressing plate 44d. The first pressing plate 44b is fixed to an inner side surface of the holder body 32a which faces the second tube holder 34, and has a pressing end surface 44a which horizontally transverses the inner side opening of the groove 32d of the holder body 32a. The second pressing plate 44d is fixed to an inner side surface of the cover 32c which faces the second tube holder 34, and has a pressing end surface 44c which is horizontally positioned when the cover 32c is located in the closed position.

When the cover 32c is located in the closed position, a gap is formed between the pressing end surface 44a of the first pressing plate 44b and the pressing end surface 44c of the second pressing plate 44d. The gap has a height that it sufficiently flatten and close the inner holes of the tubes 36 and 38.

As shown in FIG. 6, like the first tube holder 32, the second tube holder 34 also has a holder body 34a which holds the two tubes 36 and 38, and a cover 34c which is attached by a hinge (not shown) to a rear end portion of the holder body 34a to be freely rotatable relative to an upper surface of the holder body 34a between an open position and a closed portion. On the upper surface of the holder body 34a, a groove 34d is formed. The groove 34d has a U-shaped cross section, and serves as a tube holding portion which holds the two tubes 36 and 38 in a state that the two tubes 36 and 38 are stacked vertically with their peripheral surfaces being in contact with each other.

The width of the groove 34d is also preferably equal to the maximum width of each of the tubes 36 and 38, which is obtained when each of these tubes is pressed.

In the open position, as shown in FIG. 6, the cover 34c is spaced apart from an upper surface of the holder body 34a to open an upper opening of the groove 34d. In the closed position, the cover 34c is overlaid on the upper surface of the holder body 34a to close the upper opening of the groove 34d. The cover 34c may be selectively urged to the open position or the closed position by a well know selection urging means (not shown) such as a toggle spring. Also, the cover 34c may be selectively temporarily fixed at the open position or the closed position by a well known temporarily fixing means (not shown).

In this embodiment, the cover 34c is provided with locking means 46 for locking the cover 42c at the closed position. The locking means 46 has a locking plate 46b, a locking claw 46c, and a claw engaging member 46d. The locking plate 46b is attached by a hinge 46a to a free end of the cover 34c to be freely rotatable. The locking claw 46c is provided on an inner surface of the locking plate 46b. The claw engaging member 46d is provided on a front surface of the holder body 34a.

Moreover, in this embodiment, the cover 32c is provided with flattening means 48 for pressing and flattening the two tubes 36 and 38 which are held in the groove 34d of the holder body 34a of the second tube holder 34, at an inner opening of the groove 34d which faces the first tube holder 32, in the upper and lower directions so as to close the inner hole of each of the tubes 36 and 38.

The flattening means 48 has a first pressing plate 482b and a second pressing plate 48d. The first pressing plate 48b is fixed to an inner side surface of the holder body 34a which faces the first tube holder 32, and has a pressing end surface 48a (shown in FIGS. 11 to 15 to be described later), which horizontally transverses the inner side opening of the groove 34d of the holder body 34a. The second pressing plate 48d is fixed to an inner side surface of the cover 34c which faces to the first tube holder 32, and has a pressing end surface 48c which is horizontally positioned when the cover 34c is located in the closed position.

When the cover 34c is located in the closed position, a gap is formed between the pressing end surface 48a of the first pressing plate 48b and the pressing end surface 48c of the second pressing plate 48d. The gap has a height that is sufficiently flatten and close the inner holes of the tubes 36 and 38, similar to the case of the pressing means 44 of the first tube holder 32 described with reference to FIG. 8.

In this embodiment, as shown in FIG. 7, the first tube holder 32 is fixed to a frame 50, and the second tube holder 34 is supported by the frame 50 through the tube holder displacing means 41.

In an initial state of the tube connecting apparatus 30 (that is, a state before a start of an operation of the connector 30), as shown in FIG. 6, the second tube holder 34 is arranged relative to the first tube holder 32 to align the groove 34d of the second tube holder 34 with the groove 32d of the first tube holder 32 at the same level as to each other in the vertical direction. Also, as shown in FIG. 7, the second tube holder 34 is separated from the first tube holder 32 for a predetermined distance along a center line passing a center of the groove 32d of the first tube holder 32 and a center of the groove 34d of the second tube holder 34.

The tube holder displacing means 41 has a holder rotating mechanism 52 and a holder approaching mechanism 54. The holder rotating mechanism 52 is used to selectively rotate the second tube holder 34 relative to the first tube holder 32. The holder approaching mechanism 54 is used to approach and separate the second tube holder 34 to and from the first tube holder 32.

In the frame 50, a rotation driving shaft 60 is provided under the first and second tube holders 32 and 34. The rotation driving shaft 60 is extended to be parallel to the center line passing through the centers of the grooves 32d and 34d. The rotation driving shaft 60 is coupled to well known shaft rotating means 62 such as a motor, and is supported by bearings 63 on the frame 50 to be freely rotatable.

The holder approaching mechanism 54 has a cam member 64 which is coaxially fixed to the rotation driving shaft 60. On the peripheral surface of the cam member 64, a first cam groove 64a is formed to extend one time over the peripheral surface. Each of two inner side surfaces of the first cam groove 64a is positioned in an imaginary plane crossing at right angles to the rotation driving shaft 60. On that inner side surface of the groove 64a, which is close to the first tube holder 32, a cam depression 64b having a predetermined shape is formed from one predetermined rotational angel position and the other in its circumferential direction. The cam depression 64b has a bottom surface portion and a pair of inclined surface portions. The bottom surface portion extends to be parallel to the corresponding inner side surface for a predetermined length, and the pair of the inclined surface portions extend from the both ends of the bottom surface portion toward the corresponding inner side surface to make the distance between these inclined surface portions become large. The cross point where one of the inclined surface portions crosses the corresponding inner side surface, the cross points where both inclined surface portions cross the bottom surface portion, and the cross point where another inclined surface portion crosses the corresponding inner side surface are operation changing positions J, K, L and M for the holder approaching mechanism 54.

The holder approaching mechanism 54 further has a moving table 66 arranged at a side of the second tube holder 34, which is opposite to the first tube holder 32. In the frame 50, the moving table 66 is supported by a well known supporting means (not shown) to be movable in parallel to the center line of the grooves 32d and 34d.

The moving table 66 has a cam follower 66a which slidably contacts the two inner side surfaces of the first cam groove 64a of the cam member 64, and urging means 68 which is provided between the frame 50 and the moving table 66 to urge the moving table 66 toward the first tube holder 32.

The holder rotating mechanism 52 has a motor 52a and a crank shaft 52b. The motor 52a is supported by the moving table 66 to face an outer side surface of the second tube holder 34, which is opposite to the first tube holder 32. The crank shaft 52b is coupled to an output shaft of the motor 52a. As shown in FIGS. 7 and 8, the output shaft of the motor 52a is arranged to be coaxial with a straight line 70 which passes through an intermediate position between the tubes 36 and 38 pressed and flattened by the flattening means 44 in the groove 32d of the first tube holder 32, and also passes through an intermediate position between the tubes 36 and 38 pressed and flattened by the flattening means 48 in the groove 34d of the second tube holder 34. The extending end of the crank shaft 52b is fixed to the outer side surface of the second tube holder 34, which is opposite to the first tube holder 32.

Any motor which can selectively rotates its output shaft through 180° in one direction and the other direction can be used as the motor 52a. For this reason, a DC motor or a step motor, each of which is capable of controlling the rotation angle of the output shaft, is preferably used as the motor 52a.

As shown in particularly FIG. 9, the cutting means 40 has a cutting blade 40a which is located between the first and second tube holders 32 and 34 arranged in the frame 50 as mentioned above. The cutting blade 40a is supported by cutting blade displacing means 72 which is located under the cutting blade 40a in the frame 50. The blade displacing means 72 selectively reciprocates the cutting blade 40a between a cutting position and a retracted position. In the cutting position, the cutting blade 40a intersects with the tubes 36 and 38 in a space between the first and second tube holders 32 and 34. In the retracted position, the cutting blade 40a moves downward from the tubes 36 and 38 in the space between the first and second tube holders 32 and 34.

In this embodiment, the cutting blade 40a is a self-heat generating type, and is structured by, for example a two folded copper plate sandwiching an electric resistance through an insulating material. The electric resistance is connected to an electric power source 40b.

The cutting blade 40a is preferably replaced with new one at every time when it is used in one tube cutting work.

The cutting blade 40a may be heated by an outer heating means such as an electric heater or a high frequency heating means.

The cutting blade displacing means 72 has a cutting blade supporting member 72c, a cutting blade guiding member 72d, a second cam groove 64c, and a cam follower 72e. The cutting blade supporting member 72c detachably holds the cutting blade 40a and is coupled by a hinge 72b to a rotation base 72a to be rotatable in up and down directions. The rotation base 72a is fixed to the frame 50. The cutting blade guiding member 72d hangs down from the cutting blade supporting member 72c to face an inner side surface of the cam member 64 which is close to the first tube holder 32. A second cam groove 64c is formed in the inner side surface of the cam member 64. The cam follower member 72c is fixed to the cutting blade guiding member 72d and is inserted into the second cam groove 64c of the cam member 64. The second cam groove 64c has five operation changing positions O, A, B, C and D.

In this embodiment, control means 80 detects the operation of the locking means 42 of the cover 32c of the first tube holder 32 and that of the locking means 46 of the cover 34c of the second tube holder 34. The control means 80 starts the operation of the shaft rotating means 62 for the cam member 64 and also starts the electric power source 40b to heat the cutting blade 40a, when the locking means 42 and 46 are located in their engaging positions as shown in FIGS. 8 and 9. Moreover, the control means 80 detects the rotation angle of the cam member 64 and controls the rotation of the output shaft of the motor 52a of the holder rotation mechanism 52 in accordance with the rotation angle of the cam member 64.

Next, a process for connecting the two tubes 36 and 38 to each other at their positions close to their extended ends by the above-structured tube connecting apparatus according to the second embodiment of this invention, with reference to FIGS. 6 to 9 and FIGS. 10 to 15.

Figure 10:
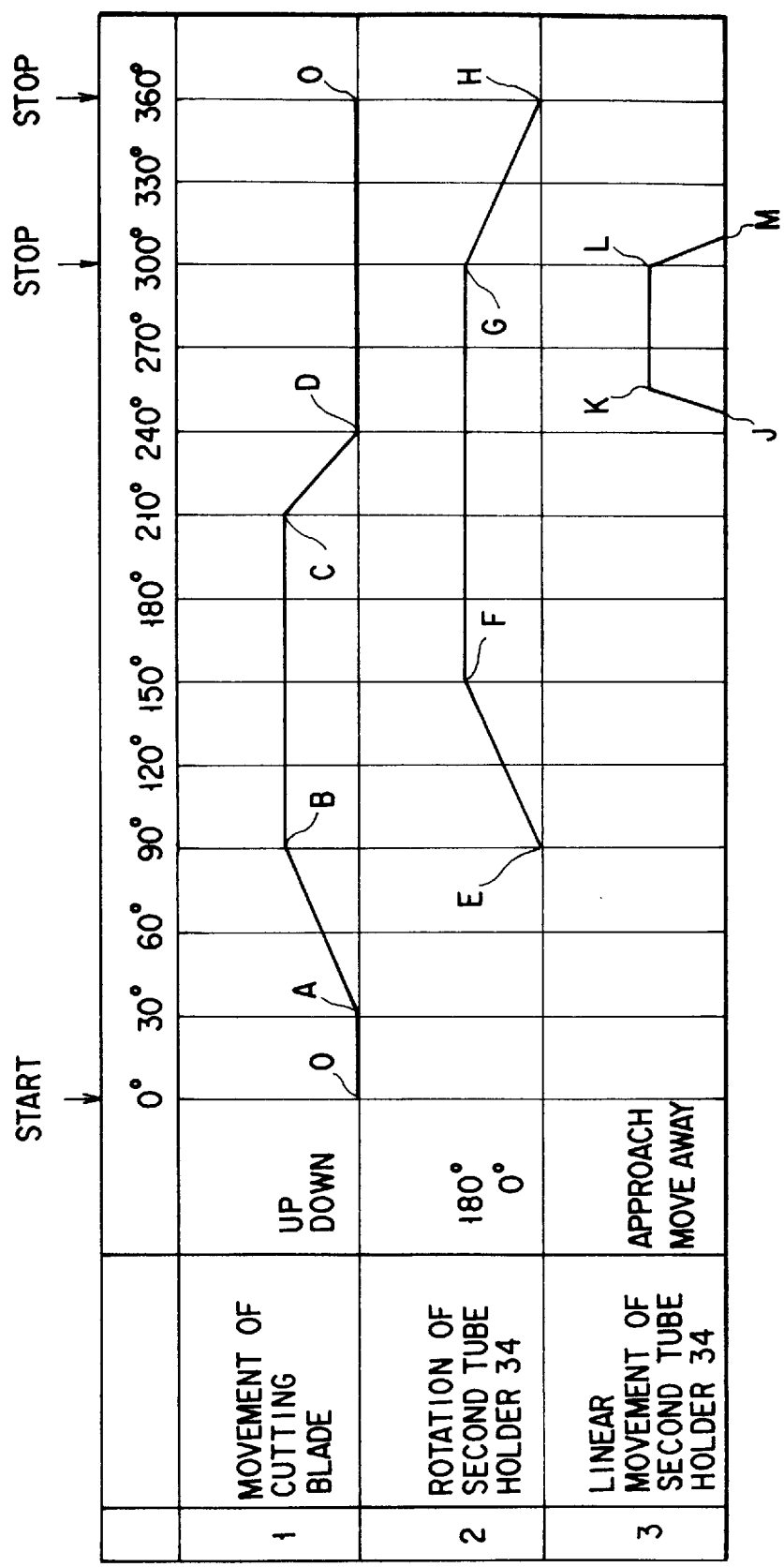
FIG. 10 is a timing chart showing timings of an operation of the cutting means of the tube connecting apparatus of FIG. 6, a revolution of a second tube holder, and approach and separation of the second tube holder to and from the first tube, in accordance with rotation angles of two cams which serve as driving sources for these operation, revolution, and approach and separation.

FIG. 10 is a timing chart showing timings of an operation of the cutting means of the tube connecting apparatus of FIG. 6, the revolution of the second tube holder 34, and approach and separation of the second tube holder 34 to and from the first tube holder 32 in accordance with the rotation angles of the two cam grooves 64a and 64b which serve as driving sources for these operation, revolution, and approach and separation. FIGS. 11 to 15 are sectional views each schematically showing a tube mounted state, a tube cut preparation state, a tube cut finish state, a tube rotated and connected state, and a tube connection finish state, in the tube connecting process which uses the tube connecting apparatus of FIG. 6.

Figure 11:
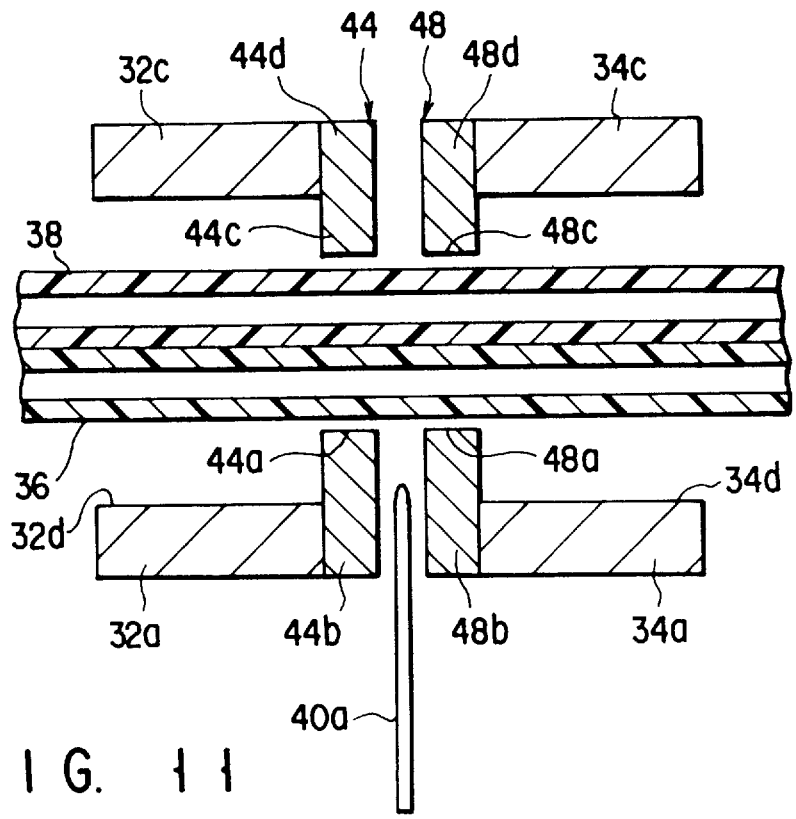
FIG. 11 is a sectional view schematically showing a tube mounted state of the main part in the tube connecting process which uses the tube connecting apparatus of FIG. 6.

While the covers 32c and 34c of the first and second tube holders 32 and 34 are located in their open positions as shown in FIG. 6, and the cutting blade 40a of the cutting means 40 is located in the lower position (retracted position) as shown in FIG. 9, the extended end portions of the two tubes 36 and 38 are inserted into the grooves 32d and 34d of the first and second tube holders 32 and 34 with their extended ends being overlapped or stacked with each other, as shown in FIG. 11. Then, a main body of the first tube 36 is extended from the first tube holder 32 in a direction opposite to the second tube holder 34, and a main body of the second tube 38 is extended from the second tube holder 34 in a direction opposite to the first tube holder 32.

In this embodiment, each of the extended end portions of the first and second tubes 36 and 38 is sealed by, for example heading and melting it.

Then, the covers 32c and 34c of the first and second tube holders 32 and 34 are rotated to their closed positions as shown in FIG. 11, and close the upper openings of the grooves 12d and 14d.

Figure 12:
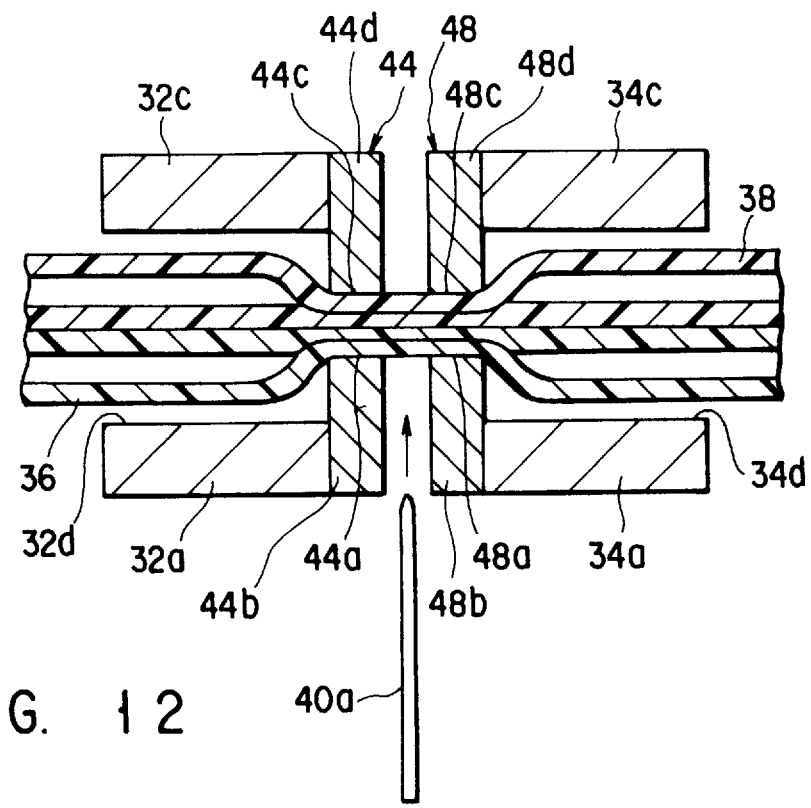
FIG. 12 is a sectional view schematically showing a tube cut preparation state of the main part in the tube connecting process which uses the tube connecting apparatus of FIG. 6.
Figure 13:
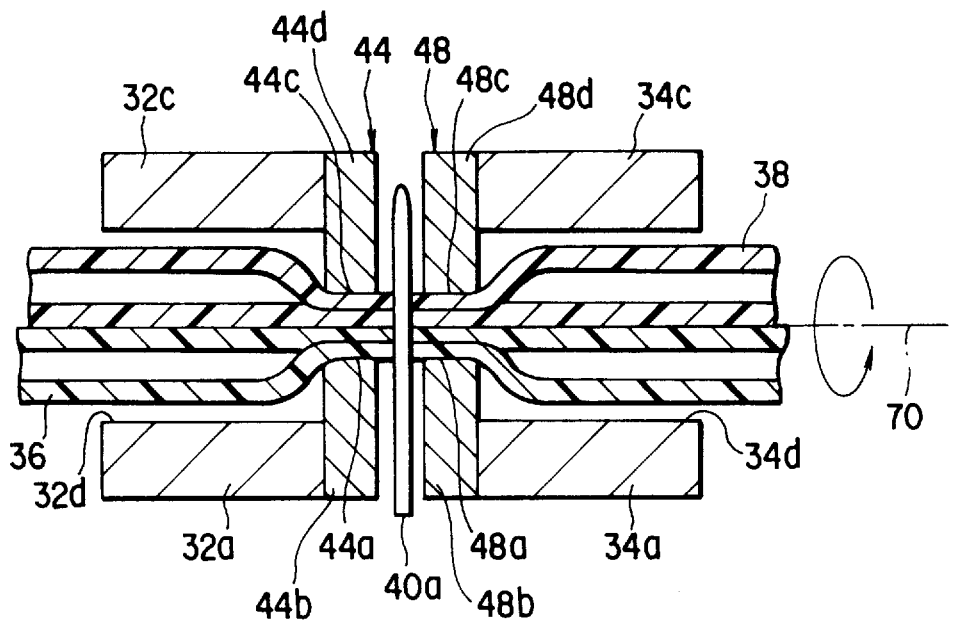
FIG. 13 is a sectional view schematically showing a tube cut finish state of the main part in the tube connecting process which uses the tube connecting apparatus of FIG. 6.

Moreover, the locking claws 42c and 46c of the locking means 42 and 46 of the first and second tube holders 32 and 34 are engaged with the claw engaging members 42d and 46d. As a result of this, as shown in FIGS. 8 and 12, the flattening means 44 of the first tube holder 32 presses the two tubes 36 and 38 from the upper and lower directions by use of the pressing end surface 44a of the first pressing plate 44b and the pressing end surface 44c of the second pressing plate 44d at the inner side opening of the groove 32d of the first tube holder 32. Then, the inner hole of each of the tubes 36 and 38 is flattened and closed by the flattening means 44 of the first tube holder 32. Moreover, the flattening means 48 of the second tube holder 34 presses the two tubes 36 and 38 from the upper and lower directions by use of the pressing end surface 48a of the first pressing plate 48b and the pressing end surface 48c of the second pressing plate 48d at the inner side opening of the groove 34d of the second tube holder 34. Then, the inner hole of each of the tubes 36 and 38 is also flattened and closed by the flattening means 48 of the second tube holder 34.

At this time, the straight line 70 which passes through the intermediate position between the two tubes 36 and 38 pressed and flattened by the flattening means 44 in the groove 32d of the first tube holder 32 and also passes through the intermediate position between the two tubes 36 and 38 pressed and flattened by the flattening means 48 in the groove 34d of the second tube holder 34, is arranged coaxial with the output shaft of the motor 52a of the holder rotation mechanism 52.

When the locking means 42 and 46 of the covers 32c and 34c of the first and second holders 32 and 34 are located in their engaging positions as shown in FIGS. 8 and 9, the controlling means 80 of FIG. 7 turns on the electric power source 40b to heat the cutting blade 40a of the cutting means 40, and also turns on the shaft rotating means 62 to rotate the cam member 64 in a predetermined direction at a predetermined speed. A start position of the cam follower 72e of the cutting blade displacing means 72 in the second cam groove 64c is indicated by a reference mark "0." Then, a voltage of, e.g., about 15 V to 24 V is applied to the cutting blade 40a from the electric power source 40b to heat the cutting blade 40a to a temperature which is more than a melting temperature of each of the tubes 36 and 38 (for example, about 260° C. to 320° C.).

When the cam member 64 rotates through 30° counterclockwise from the starting position "O" shown in FIG. 9, the cam follower 72e of the cutting blade displacing means 72 reaches a rise starting position indicated by a reference mark "A" in the second cam groove 64c of the cam member 64, and starts to move up the cutting blade 40a of the cutting means 40 from the retracted position which is shown by FIGS. 9 and 12, by the cutting blade displacing means 72.

The rise of the cutting blade 40a by the cam follower 72e continues till the cam member 64 rotates through 90° counterclockwise from the start position "O" shown in FIG. 9 and the cam follower 72e of the cutting blade displacing means 72 reaches a rise finish position indicated by a reference mark "B" in the second cam groove 64c of the cam member 64.

Figure 14:
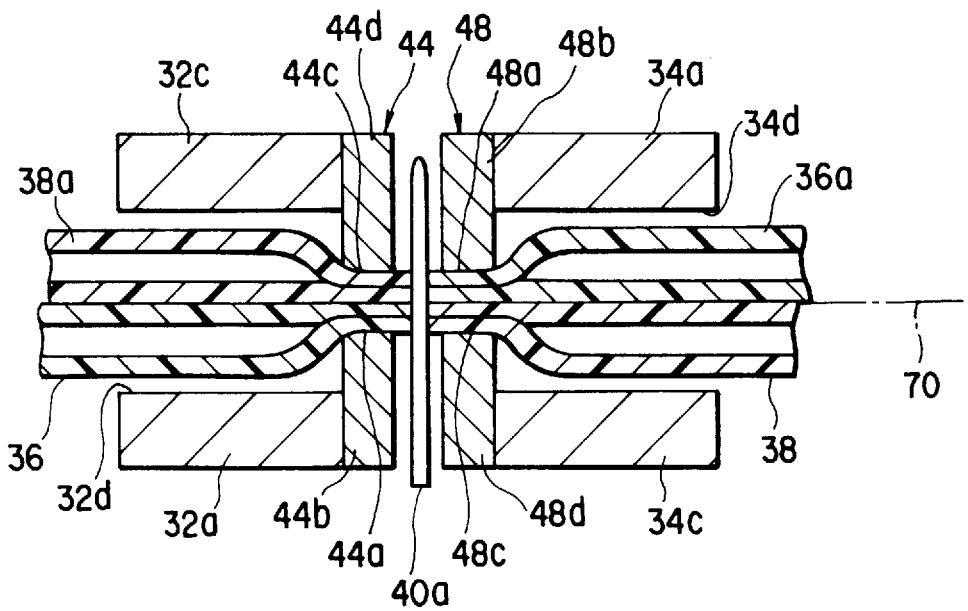
FIG. 14 is a sectional view schematically showing a tube rotated and connected state of the main part sequent to the tube cut finish state of FIG. 13 in the tube connecting process which uses the tube connecting apparatus of FIG. 6.

During this time, as shown in FIG. 14, the cutting blade 40a in rose up to the cutting position in which the cutting blade 40a crosses the tubes 36 and 38 pressed and flattened by the flattening means 44 and 48, in the gap between the first and second tube holders 32 and 34, so that the cutting blade 40a melts the pressed two tubes 36 and 38 to cut them.

While the cam member 64 rotates from the 90° rotation angle position to 210° rotation angle position counterclockwise in a state that the starting position "O" shown in FIG. 9 is set as a reference, the cam follower 72e maintains the cutting blade 40e at the cutting position as shown in FIG. 14.

When the cam member 64 rotates through 90° counterclockwise from the starting position "O" shown in FIG. 9, the controlling means 80 of FIG. 7 controls the motor 52a of the holder rotating mechanism 52 to start the rotation of the crank shaft 52b at a predetermined speed in a counterclockwise direction which is seen from the right side in FIG. 7.

The rotation of the crank 52b by the motor 52a of the holder rotating mechanism 52 continues while the cam member 64 rotates from the 90° rotation angle position to the 150° rotation angle position. During this time, as shown in FIG. 14, the crank shaft 52b rotates through 180° so that the second tube holder 34 is revolved through 180°.

The longitudinal center line of the crank shaft 52b, that is, the longitudinal center line of the output shaft of the motor 52a, is aligned to the straight line 70 passing through the intermediate position between the tubes 36 and 38 which are depressed and flattened by the flattening means 44 in the groove 32d of the first tube holder 32, and also passing through the intermediate position between the tubes 36 and 38 which are depressed and flattened by the flattening means 48 in the groove 32d of the second tube holder 34. Therefore, after this rotation, the cutting end of the main body of the second tube 38 which is depressed and flattened by the flattening means 48 in the groove 34d of the reversed second tube holder 34, is arranged to be aligned with the cutting end of the main body of the first tube 36 which is depressed and flattened by the flattening means 44 in the groove 32d of the first tube holder 32. Also, the cutting end of the extended end portion 36a of first tube 36 which is depressed and flattened by the flattening means 48 in the groove 34d of the reversed second tube holder 34, is arranged to be aligned with the cutting end of the extended end portion 38a of the second tube 38, which is depressed and flattened by the flattening means 44 in the groove 32d of the first tube holder 32.

The 180° rotation of the crank 52b by the motor 52a of the holder rotating mechanism 52, that is, the 180° revolution of the second tube holder 34, starts at a time when the cam member 64 rotates through 150° counterclockwise from the starting position "O" shown in FIG. 9, and ends at a time when the cam member 64 rotates through 300° from the starting position "O".

When the cam member 64 rotates through 210° counterclockwise from the starting position "O" shown in FIG. 9, and the cam follower 72e of the cutting blade displacing means 72 reaches the descent starting position indicated by a reference mark "C" in the second cam groove 64c of the cam member 64, the cam follower 72e moves down the cutting blade 40a of the cutting means 40 from the upper position (cutting position) shown in FIG. 14 to the lower direction (retracted position) shown in FIG. 9 or FIG. 11.

The descent or downward movement of the cutting blade 40a by the cam follower 72e continues till the cam member 64 rotates through 240° counterclockwise from the start position "O" shown in FIG. 9, so that the cam follower 72e of the cutting blade displacing means 72 reaches at a descent finish position indicated by a reference mark "D" in the second cam groove 64c of the cam member 64.

In other words, the downward movement of the cutting blade 40a from the upper position (cutting position) shown in FIG. 14 to the lower direction (retracted position) shown in FIG. 9 or FIG. 11 is performed while the second tube holder 34 is kept in the 180° reversed position. As a result, the melted cutting end of the main body of the first tube 36 which is depressed and flattened by the flattening means 44 in the groove 32d of the first tube holder 32, directly comes in contact with the melted cutting end of the main body of the second tube 38 which is depressed by the flattening means 48 in the groove 34d of the reversed second tube holder 34. Also, the melted cutting end of the extended end portion 38a of the second tube 38 which is depressed and flattened by the flattening means 44 in the groove 32d of the first tube holder 32, directly comes in contact with the melted cutting end of the extended end portion 36a of first tube 36 which is depressed and flattened by the flattening means 48 in the groove 34d of the reversed second tube 34.

While the cam member 64 rotates counterclockwise from a 240° rotation angle position at which the cam follower 72e of the cutting blade displacing means 72 reaches a descent finish position indicated by a reference mark "D" in the second cam groove 64c of the cam member 64, to a 360° rotation angle position at which the cam follower 72e reaches a rotation finish position indicated by a reference "O" in the second cam groove 64c, the cam follower 72e maintains the cutting blade 40a of the cutting means 40 at the lower position (retracted position) by the cutting blade displacing means 72.

When the cam member 64 is rotated through 250° counterclockwise from the starting position "O" shown in FIG. 9, the cam follower 66a of the moving table 66 of the holder approaching mechanism 54 reaches an approaching start position (indicated by a reference mark "J") in the cam depression 64b in the first cam groove 64a of the cam member 64 shown in FIG. 7.

When the cam member 64 rotates through 260° counterclockwise from the starting position "O" shown in FIG. 9, the moving table 66 of the holder approaching mechanism 54 which is urged toward the first tube holder 32 by the urging means 68, makes the cam follower 66a reach an approaching maintain start position indicated by a reference mark "K" in the cam depression 64b in the first cam groove 64a of the cam member 64 as shown in FIG. 7, so that the second tube holder 34 is made to approach the first tube holder 32.

The approach of the second tube holder 34 to the first tube holder 32 continues till the cam member 64 rotates through 300° counterclockwise from the starting position "O" shown in FIG. 9 and the cam follower 66a of the moving table 66 of the holder approaching mechanism 54 reaches an approaching maintain finish position indicated by a reference mark "L" in the cam depression 64b in the first cam groove 64a of the cam member 64 shown in FIG. 7.

In other word, the approach of the second tube holder 34 to the first tube holder 32 is performed while the second tube holder 34 is reversed at 180° relative to the first tube holder 32 and just after the cutting blade 40a is moved down from the upper position (cutting position) shown in FIG. 14 to the lower direction (retracted position) shown in FIG. 9 or FIG. 11.

Figure 15:
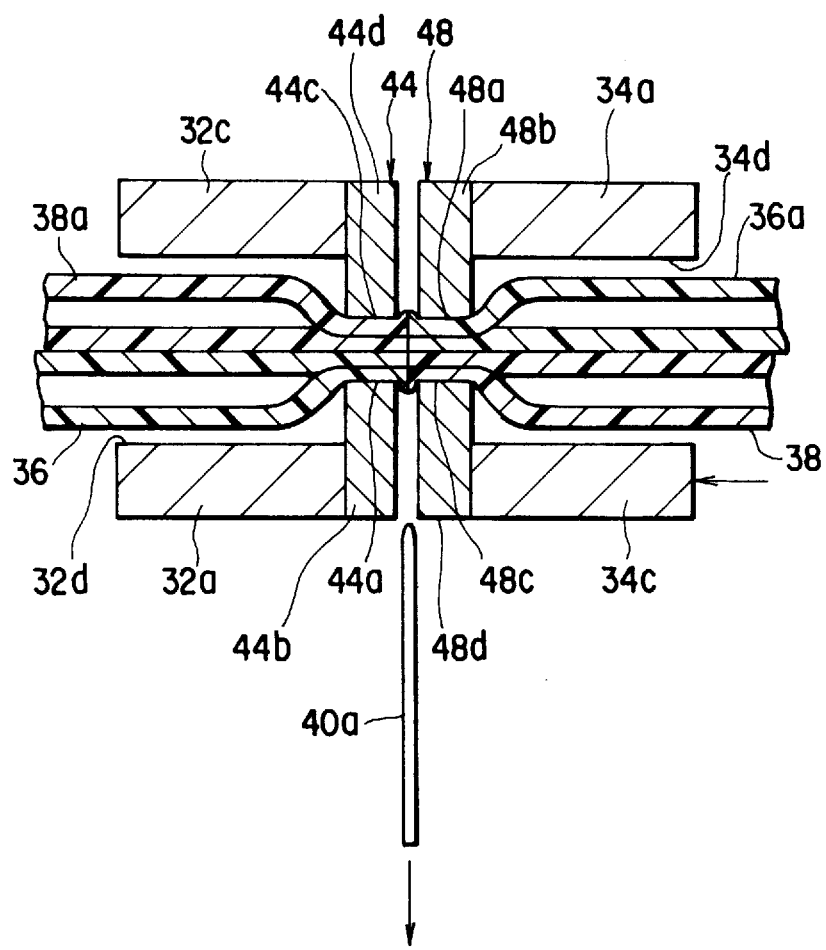
FIG. 15 is a sectional view schematically showing a tube connection finish state of the main part sequent to the tube rotated and connected state of FIG. 14 in the tube connecting process which uses the tube connecting apparatus of FIG. 6.

As a result of this, the direct contact and connection between the cutting end of the main body of the first tube 36 which is depressed and flattened by the flattening means 44 in the groove 32d of the first tube 32, and the cutting end of the main body of the second tube 38 which is depressed and flattened by the flattening means 48 in the groove 34d of the reversed second tube 34, is performed under the urging force of the urging means 68, and the connection is reinforced. Also, the direct contact and connection between the cutting end of the extended end portion 38a of the second tube 38 which is depressed and flattened by the flattening means 44 in the groove 32d of the first tube 32, and the cutting end of the extended end portion 36a of the first tube 36 which is depressed and flattened by the flattening means 48 in the groove 34d of the reversed second tube 34, is performed under the urging force of the urging means 68, and the connection is reinforced. This state is shown in FIG. 15.

Each of the connection between the cutting end of the main body of the first tube 36 and the cutting end of the main body of the second tube 38, and the connection between the cutting end of the extended end portion 38a of the second tube 38 and the cutting end of the extended end portion 36a of the first tube 36, is performed in a state that each cutting end is depressed and flattened and each inner hole of the main bodies and the extended end portions 36a and 38a of the two tubes 36 and 38 is closed. Therefore, even if liquid exists in the inner hole of each of the tubes 36 and 38 before they are cut and connected, no liquid is leaked out from the inner hole of each of the tubes 36 and 38 during the connecting process as described above.

Moreover, the cutting end of the main body of the first tube 36 and the cutting end of the main body of the second tube 38 are set in a high temperature state such as a melting or softening state, and these cutting ends are covered by the cutting blade 40a of high temperature, from the time at which the two tubes 36 and 38 are cut to the time at which the two tubes 36 and 38 are contacted and connected to each other. Therefore, the above described connecting process is performed in a sterile state.

The rotation of the cam member 64 in the counterclockwise direction at a predetermined speed from the starting position "O" shown in FIG. 9 is temporarily stopped when the cam member 64 is rotated through 300° counterclockwise. At this time, as described above, the cutting blade 40a of the cutting means 40 is held at the lower position (retracted position) shown in FIG. 9 or 11, by the cutting blade displacing means 72, the second tube holder 34 is reversed through 180° relative to the first tube holder 32 by the crank shaft 52b of the motor 52a of the holder rotation mechanism 52 as shown in FIG. 15, and the second tube holder 34 is approached to the first tube holder 32 by the moving table 66 of the holder rotation mechanism 52.

During this time, the engagement of the locking means 42 with the holder body 32a of the first tube holder 32 is released, so that the cover 32c of the first tube holder 32 is moved to the open position as shown in FIG. 6. Thereafter, the main bodies of the two tubes 36 and 38 connected each other and the extended end portions 36a and 38a of the two tubes 36 and 38 connected each other are taken out from the groove 32d of the first tube holder 32.

Next, the locking means 42 is engaged with the holder body 32a of the first tube holder 32 again so as to locate the cover 32c of the first tube holder 32 in the closed position again. Thereafter, the controlling means 80 controls the shaft rotating means 62 to rotate the rotation driving shaft 60 in the predetermined direction at the predetermined speed again. Then, the counterclockwise rotation of the cam member 64 is stopped when the cam member 64 rotates through 360° from the starting position "O" shown in FIG. 9 and is returned to the initial position as shown in FIG. 10.

During this time, when the cam member 64 rotates counterclockwise from a 300° rotation angle position to a 310° rotation angle position, the cam follower 66a of the moving table 66 of the holder approaching mechanism 54 is returned against the urging force of the urging means 68 of the moving table 66 from the approach maintain finish position to a return finish position in the cam depression 64b of the first cam groove 64a of the cam member 64 shown in FIG. 7. In this case, the approach maintain finish position is indicated by a reference mark "L" in the cam depression 64b. The return finish position is indicated by a reference mark "M." Thereafter, while the cam member 64 rotates up to 360° counterclockwise from the starting position "O" shown in FIG. 9, the cam follower 66a of the moving table 66 of the holder approaching mechanism 54 is maintained at the return finish position in the first cam groove 64a of the cam member 64 shown in FIG. 7.

Moreover, while the cam member 64 starts to rotate again counterclockwise from the 300° rotation angle position to the 360° rotation angle position or to the initial starting position, the controlling means 80 of FIG. 7 controls the motor 52a of the holder rotating mechanism 52 to rotate the crank shaft 52b through 180° in a clockwise direction which is seen from the right side in FIG. 7, at a predetermined speed. As a result, the second tube holder 34 is returned to the initial state as shown in FIG. 6 from the state that the second tube holder 34 is reversed through 180° relative to the first tube holder 32.

Finally, the engagement of the locking means 48 with the holder body 34a of the second tube holder 34 is released, so that the cover 34c of the second tube holder 32 is located in the open position as shown in FIG. 6. Thereafter, the main bodies of the tubes 36 and 38 connected each other and the extended end portions 36a and 38a of the tubes 36 and 38 connected each other are taken out from the groove 34d of the second tube holder 34.

Since the extended end portions 36a and 38a of the tubes 36 and 38 connected each other are unnecessary, they are discarded. In this case, since these extended end portions 36a and 38a are connected each other, a possibility that the discarded these extended end portions 36a and 38a will be scattered around the tube connecting apparatus can be reduced as compared with a case in which the extended end portions 36a and 38a of the tubes 36 and 38 are not connected each other.

The main bodies of the tubes 36 and 38 connected each other and the extended end portions 36a and 38a connected each other can be taken out from the grooves 32d and 34d of the first and second tube holders 32 and 34 as follows.

At first, while the rotation of the cam member 64 is stopped after the cam member 64 rotates through 300° counterclockwise from the starting position "O" shown in FIG. 9, the engagement of the locking means 42 with the holder body 32a of the first tube holder 32 and the engagement of the locking means 48 with the holder body 34a of the second tube holder 32 are released. As a result, the cover 32c of the first tube holder 32 and the cover 34c of the second tube holder 34 are located in the open positions, respectively, as shown in FIG. 6. Thereafter, the main bodies of the tubes 36 and 38 connected each other and the extended end portions 36a and 38a of the tubes 36 and 38 connected each other are taken out from both of the groove 32d of the first tube holder 32 and the groove 34d of the second tube holder 34.

In this case, the cutting blade 40a which have been located in the descent or lower position (retracted position) of FIG. 4, does not prevent the main bodies of the tubes 36 and 38 connected each other and the extended end portions 36a and 38a of the tubes 36 and 38 connected each other from being taken out from the grooves 32d and 34d.

Finally, the locking means 42 is engaged with the holder body 32a of the first tube holder 32 again. Also, the locking means 48 is engaged with the holder body 34a of the second tube holder 34 again. As a result, the cover 32c of the first tube holder 32 and the cover 34c of the second tube holder 34 are located in their closed positions. Then, the controlling means 80 controls the shaft rotating means 62 to rotate the rotation driving shaft 60 in the predetermined direction at the predetermined speed again. And, the counterclockwise rotation of the cam member 64 is stopped when the cam member 64 is rotated through 360° from the staring position "O" shown in FIG. 9 and is returned to the initial starting position as shown in FIG. 10.

During this time, when the cam member 64 rotates counterclockwise from the 300° rotation angle position to the 310° rotation angle position, the cam follower 66a of the moving table 66 of the holder approaching mechanism 54 is returned against the urging force of the urging means 68 of the moving table 66 from the approach maintain finish position to the return finish position in the first cam groove 64a of the cam member 64 shown in FIG. 7. In this case, the approach maintain finish position is indicated by the reference mark "L" in the cam depression 64b. The return finish position is indicated by the reference mark "M." Thereafter, while the cam member 64 rotates up to 360° counterclockwise from the starting position "O" shown in FIG. 9, the cam follower 66a of the moving table 66 of the holder approaching mechanism 54 is maintained at the return finish position in the first cam groove 64a of the cam member 64 shown in FIG. 7.

Moreover, while the cam member 64 starts to rotate counterclockwise again from the 300° rotation angle position and returns to the 360° rotational angle position or the initial starting position, the controlling means 80 of FIG. 7 controls the motor 52a of the holder rotating mechanism 52 to rotate the crank shaft 52b through 180° in the clockwise direction which is seen from the right side in FIG. 7, at the predetermined speed. As a result, the second tube holder 34 is returned to the initial state as shown in FIG. 6 from the state that the second tube holder 34 is reversed through 180° relative to the first tube holder 32.

The first and second embodiments are described to make this invention being understood easily, so that this invention in its broader aspect is not limited to the first and second embodiments, and this invention is defined only by the description in claims attached hereto. Accordingly, various modifications may be made without departing from the spirit or scope of this invention defined by the appended claims.

In the first and second embodiments, the displacement of the second tube holder relative to the first tube holder was performed by the revolution of the second tube holder which is concentric with the first tube holder, to contact the cut ends of the main bodies of the tubes 36 and 38 each other. However, for example, the second tube holder may be linearly moved along the inner side surface of the first tube holder to contact the cut ends of the main bodies of the tubes 36 and 38 each other.

Moreover, the number of tubes to be contacted and connected may be more than two. For bringing each of cutting ends of the tubes in contact with a desirable opponent, the displacement of the second tube holder relative to the first tube holder can be performed by a combination of the revolution of the second tube holder which is concentric with the first tube holder, and the linear movement of the second tube holder along the inner side surface of the first tube holder, if necessary. Furthermore, for holding the plurality of tubes with their peripheral surfaces being contacted each other, it is possible to use suitable holding means provided in the first and second tube holders in place of the grooves described in the first and second embodiments.

What is claimed is:

1. A tube connecting apparatus comprising:
   first and second tube holders for holding a plurality of flexible tubes, each tube holder including a tube holding portion having a groove which possesses a width that is substantially the same as that of each tube and into which the tubes are received and held in a stacked state so that peripheral surfaces of the tubes contact each other;
   a cutting device which heats, melts, and cuts the tubes held by the first and second tube holders at a position between the first and second tube holders; and
   a tube holder displacing device which displaces the second tube holder relative to the first tube holder after the tubes held by the first and second tube holders are cut by the cutting device at a location between the tube holders, and connects cut ends of the tubes held by the second tube holder to cut ends of the tubes held by the first tube holder.

2. A tube connecting apparatus according to claim 1, wherein said tube holder displacing device includes a holder rotating mechanism which rotates said second tube holder relative to said first tube holder on a center line which passes through an intermediate position of the plurality of tubes held by each holder and which extends in a direction of longitudinal extent of the plurality of tubes.

3. A tube connecting apparatus according to claim 2, wherein said tube holder displacing device revolves said second tube holder relative to said first tube holder through 180°, so that the cut ends of the plurality of tubes held in said second tube holder rotate on the center line through 180° relative to the cut ends of the plurality of tubes of said first tube holder to be aligned with each other.

4. A tube connecting apparatus according to claim 1, wherein said tube holder displacing device has a holder approaching mechanism which reduces the distance between said first and second tube holders after said second tube holder is revolved relative to said first tube holder through 180°.

5. A tube connecting apparatus according to claim 1, wherein said cutting device includes a cutting blade heated at a high temperature for melting and cutting the plurality of tubes, and a cutting blade moving device which inserts and retracts said cutting blade into and out of a gap between said first and second tube holders.

6. A tube connecting apparatus according to claim 1, wherein each of the first and second tube holders includes a tube flattening device which flattens the tubes held by the groove of each of the tube holders to close an inner hole in each of the tubes.

7. A tube connecting apparatus comprising:
   a first tube holder and a second tube holder, the first and second tube holders each having a groove for receiving a plurality of flexible tubes, the groove of the first tube holder being aligned with the groove of the second tube holder;
   a cutting device for heating, melting and cutting the tubes held in the groove of the first tube holder and the groove of the second tube holder at a position between the first and second tube holders; and
   a tube holder displacing device for displacing the second tube holder relative to the first tube holder about an axis extending through the groove in the second tube holder after the tubes have been cut by the cutting device at a position between the first and second tube holders and for effecting connection of cut ends of the tubes held in the groove of the second tube holder to cut ends of the tubes held in the groove of the first tube holder.

8. A tube connecting apparatus according to claim 7, wherein each of the first and second tube holders includes a tube flattening device which flattens the tubes held by the groove of each of the tube holders to close an inner hole in each of the tubes.

9. A tube connecting apparatus according to claim 7, wherein the tube holder displacing device includes a motor having an output shaft, said output shaft being coaxial with a center line of the groove in the second tube holder.

10. A method for cutting tubes and connecting together cut ends of the tubes comprising:

placing a first tube in a groove in a first tube holder and in a groove in a second tube holder so that the first tube is located in and extends between the groove in the first tube holder and the groove in the second tube holder;

placing a second tube in said groove in the first tube holder and in said groove in the second tube holder so that the second tube is located in and extends between the groove in the first tube holder and the groove in the second tube holder and so that the first and second tubes are in stacked relation to one another;

melting and cutting the first and second tubes at a location between the first and second tube holders to produce first and second cut ends on both the first and second tubes;

displacing the second tube holder relative to the first tube holder; and connecting the first cut end of the first tube to the second cut end of the second tube.

11. A method according to claim 10, including connecting the second cut end of the first tube to the first cut end of the second tube.

12. A method according to claim 10, wherein the second tube holder is displaced relative to the first tube holder by rotating the second tube holder about an axis passing through said groove in the second tube holder.

13. A method according to claim 10, wherein each of the tubes includes an inner hole, and including flattening a portion of the first and second tubes to close the inner hole in the first and second tubes.

* * * * *

UNITED STATES PATENT AND TRADEMARK OFFICE
CERTIFICATE OF CORRECTION

PATENT NO. : 5,802,689

DATED : September 8, 1998

INVENTOR(S) : Hiroaki SANO

It is certified that error appears in the above-identified patent and that said Letters Patent is hereby corrected as shown below:

In Column 10, line 65, delete "482b" and insert -- 48b --.

Signed and Sealed this

Ninth Day of March, 1999

Attest:

Attesting Officer

Q. TODD DICKINSON

Acting Commissioner of Patents and Trademarks